US012623072B2

(12) United States Patent
Lee et al.

(10) Patent No.: US 12,623,072 B2
(45) Date of Patent: May 12, 2026

(54) NEGATIVE POTENTIAL GENERATION DEVICE

(71) Applicant: TAIWAN OASIS TECHNOLOGY CO.,LTD., Taipei City (TW)

(72) Inventors: Ming-Shun Lee, New Taipei City (TW); Ming-Der Lin, Hsinchu County (TW)

(73) Assignee: TAIWAN OASIS TECHNOLOGY CO. , LTD., Taipei City (TW)

( * ) Notice: Subject to any disclaimer, the term of this patent is extended or adjusted under 35 U.S.C. 154(b) by 139 days.

(21) Appl. No.: 18/748,353

(22) Filed: Jun. 20, 2024

(65) Prior Publication Data

US 2024/0424292 A1 Dec. 26, 2024

Related U.S. Application Data

(60) Provisional application No. 63/523,130, filed on Jun. 26, 2023.

(51) Int. Cl.
*A61N 1/16* (2006.01)
*H05K 5/02* (2006.01)

(52) U.S. Cl.
CPC .............. *A61N 1/16* (2013.01); *H05K 5/0217* (2013.01); *H05K 5/0247* (2013.01)

(58) Field of Classification Search
CPC ... A61N 1/16; A61N 1/00; A61N 1/02; A61N 1/18; H05K 5/0217; H05K 5/0247; H01T 19/04; H01T 23/00; H01B 17/56
(Continued)

(56) References Cited

U.S. PATENT DOCUMENTS

| | | | | |
|---|---|---|---|---|
| 4,167,301 A | * | 9/1979 | Mundschenk | ....... H02G 3/0633 |
| | | | | 439/457 |
| 7,994,436 B2 | * | 8/2011 | Yamamoto | ........... H01R 25/006 |
| | | | | 361/679.01 |

(Continued)

FOREIGN PATENT DOCUMENTS

| | | |
|---|---|---|
| CN | 206081327 B2 | 4/2017 |
| CN | 113350020 A | 9/2021 |

(Continued)

OTHER PUBLICATIONS

Title: Negative Potential Therapy device with air cleaning device; Entire specification and drawings; (Year: 2017).*

(Continued)

*Primary Examiner* — Dharti H Patel
(74) *Attorney, Agent, or Firm* — Demian K. Jackson; Jackson IPG PLLC

(57) ABSTRACT

A negative potential generating device which includes an insulating box, an AC/DC converter, a booster, a second wire and an insulating lid is presented. The insulating box has a side wall, and an inner surface of the side wall has a blind hole. The AC/DC converter is arranged inside the insulating box, and electrically connected with a plug through a first wire. The booster is arranged inside the insulating box and electrically connected with the AC/DC converter. One side of the second wire is electrically connected with the booster, another side of the second wire is exposed and inserted into the blind hole and contacts with an inner wall surface of the blind hole. The insulating lid covers the insulating box. The device is easy to carry and generates negative potential anytime and anywhere after connecting to a power supply, making it easier and more convenient to use.

7 Claims, 7 Drawing Sheets

(58) Field of Classification Search
USPC ......................................................... 361/230
See application file for complete search history.

(56)                     References Cited

U.S. PATENT DOCUMENTS

| | | | | |
|---|---|---|---|---|
| 8,522,795 | B2 * | 9/2013 | Bouix ..................... | A45D 33/26 |
| | | | | 206/349 |
| 8,941,976 | B1 * | 1/2015 | Maroney .................. | H04B 3/56 |
| | | | | 439/639 |
| 2005/0234524 | A1 * | 10/2005 | Horiguchi .............. | A61N 1/326 |
| | | | | 607/50 |
| 2013/0334024 | A1 * | 12/2013 | Chang ..................... | G06F 3/016 |
| | | | | 200/600 |
| 2015/0062769 | A1 * | 3/2015 | Cortes Rico ........... | H01H 83/02 |
| | | | | 361/93.1 |
| 2024/0120190 | A1 * | 4/2024 | Kishida ................... | H02M 3/28 |
| 2024/0431081 | A1 * | 12/2024 | Lee ....................... | H05K 9/0052 |
| 2025/0300372 | A1 * | 9/2025 | Morrow .............. | H01R 4/2407 |

FOREIGN PATENT DOCUMENTS

| | | | | | |
|---|---|---|---|---|---|
| CN | 119815818 | A | * | 4/2025 | |
| TW | 200743503 | A | | 12/2007 | |
| TW | M526410 | B2 | | 8/2016 | |
| WO | WO-2024085834 | A1 | * | 4/2024 | ............... A61G 5/10 |

OTHER PUBLICATIONS

Negative potential therapy device with air cleaning device (Year: 2017).*
Office Action with the first search report for the corresponding TW Appln. 112134397 issued at Jul. 10, 2024.

* cited by examiner

NEGATIVE POTENTIAL GENERATION DEVICE

BACKGROUND

Technical Field

The present disclosure relates to a negative potential generating device, in particular to a negative potential generating device which has health care effects on a human body.

Related Art

Recently, due to the technology development and industrial acceleration, and further due to the popularization of electronic/electrical products and compact living space, the increasing positive potential in the environment causes the potential balance in the environment to be seriously damaged. Since a current consensus is to use the negative ions to solve the problem of potential balance being destroyed, negative ion generators that artificially provides negative ions are gradually favored by public, and various related products are also popping out one after another. There are corona discharging and electron radiation types of negative ion generators. The corona discharging (also known as direct current (DC) free corona discharging) negative ion generator applies a high voltage between its negative electrode and induced electrode in the DC loop to form a strong electric field, which destroys the insulation of local air and causes corona discharging, and then the negative electrode will release negative ions. The electron radiation negative ion generator uses a piezoelectric transformer driving circuit to generate negative high voltage, and then applies the negative high voltage to a negative electrode, thereby releasing electrons to generate negative ions. However, when the above-mentioned corona discharging negative ion generator also produces excessive pollutants such as ozone and nitric oxide, which harms the human body, while producing negative ions in the air.

In order to prevent the human body from inhaling ozone and nitric oxide, a negative ion generator provided by Taiwan utility model patent No. M367722 (hereinafter referred to as Document 1) seals negative ions, ozone and nitric oxide in a wooden box, and then the human body can touch the box. Document 1 alleges that negative ions may penetrate the wooden box and be transmitted to the human body. However, negative ions are transmitted by air, and the air circulation between the wooden box and the outside is relatively low, which means that most negative ions will be sealed in the wooden box and only minority of negative ions will be transmitted to the outside, and thus the performance of releasing negative ions in Document 1 is not ideal.

Therefore, the attempt of using the negative ions to solve the potential imbalance in the environment caused by the increase of the positive potential of the environment increases the risk of generating pollutants in implementation, and to seal both the negative ions and pollutants in inner space results in poor performance of releasing negative ions.

SUMMARY OF THE INVENTION

Based on the above acknowledgement, the inventor of the present disclosure realized that negative potential has the following advantages for human body:

1. Purification of blood: If the negative potential in the body increases, the ionization of calcium and sodium in the blood will be accelerated, making the blood present weak alkalescency (the corresponding pH value is 7.4±0.05), and thus the blood can be purified.

2. Recovery of cells: When negative potential increases, the metabolism gradually becomes normal and revives, and meanwhile the function of cells will obviously improve, nutrients will be easily absorbed, and aged wastes will be easily discharged.

3. Enhancement of resistance and self-healing: When the negative potential increases, globulin in blood will also increase, and therefore the immunity to diseases increase, and the self-healing ability of human body will also increase, which can even inhibit cell inflammation and accelerate the recovery of wounds.

4. Adjustment of autonomic nerve: Almost all organs are controlled by the sympathetic nerve and parasympathetic nerve. For example, the functions of heart, vasoconstriction, pupil dilation and gastrointestinal function are all controlled by the sympathetic nerve. When the tension of sympathetic nerve increases, these functions will be enhanced, and when the tension of parasympathetic nerve increases, there will be opposite effects. These two kinds of nervous systems with opposite effects remain balanced by the autonomic nerve so that the inside environment of the human body will not be affected by the will, and the almost all organs of the human body can function automatically. The negative potential can help adjust the autonomic nerve, and when the autonomic nerve is adjusted to normal, some chronic diseases of the human body will naturally stay away.

Based on the above knowledgement as well as the fact that people are busy in daily life, it is urgent to develop a negative potential generating device that can be operated and used at any time.

The objective of the present disclosure is to provide a negative potential generating device, which is portable and can generate negative potential anytime and anywhere after being connected to a power supply, so that the operations thereof is easier and more convenient.

Another objective of the present disclosure is to provide a negative potential generating device, which can shield electromagnetic waves when the negative potential is generated, thus preventing the human body, other objects or electrical appliances from effects.

In order to solve the above problems, the present disclosure provides a negative potential generating device which comprises an insulating box, an alternating current/direct current (AC/DC) converter, a booster, a second wire and an insulating lid. The insulating box has a side wall, and an inner surface of the side wall has a blind hole. The AC/DC converter is arranged inside the insulating box, and electrically connected with a plug through a first wire. The booster is arranged inside the insulating box and electrically connected with the AC/DC converter. One side of the second wire is electrically connected with the booster, another side of the second wire is exposed and inserted into the blind hole and contacts with an inner wall surface of the blind hole. The insulating lid covers the insulating box.

In some embodiments, a space between the insulating box, the AC/DC converter and the booster is filled with a plurality of cotton threads.

In some embodiments, the insulating box and the insulating lid are made of wooden material.

In some embodiments, the insulating lid covers the insulating box, so that the insulating box is sealed and air inside the insulating box is isolated from air outside the insulating box.

In some embodiments, the AC/DC converter and the booster are fixed in the insulating box through an adhesive member.

In some embodiments, a filling or plugging member is filled or plugged between the second wire and the blind hole.

In some embodiments, another space between the insulating box, the AC/DC converter, the booster and the cotton threads is filled with grapheme.

The above objects and advantages of the present disclosure can be easily understood from the following detailed description of selected embodiments and the accompanying drawings. The present disclosure will be described in detail in the following examples with the accompanying drawings.

DESCRIPTIONS OF DRAWINGS IN THE INVENTION

DESCRIPTIONS OF EMBODIMENTS IN THE INVENTION

Figure 1:
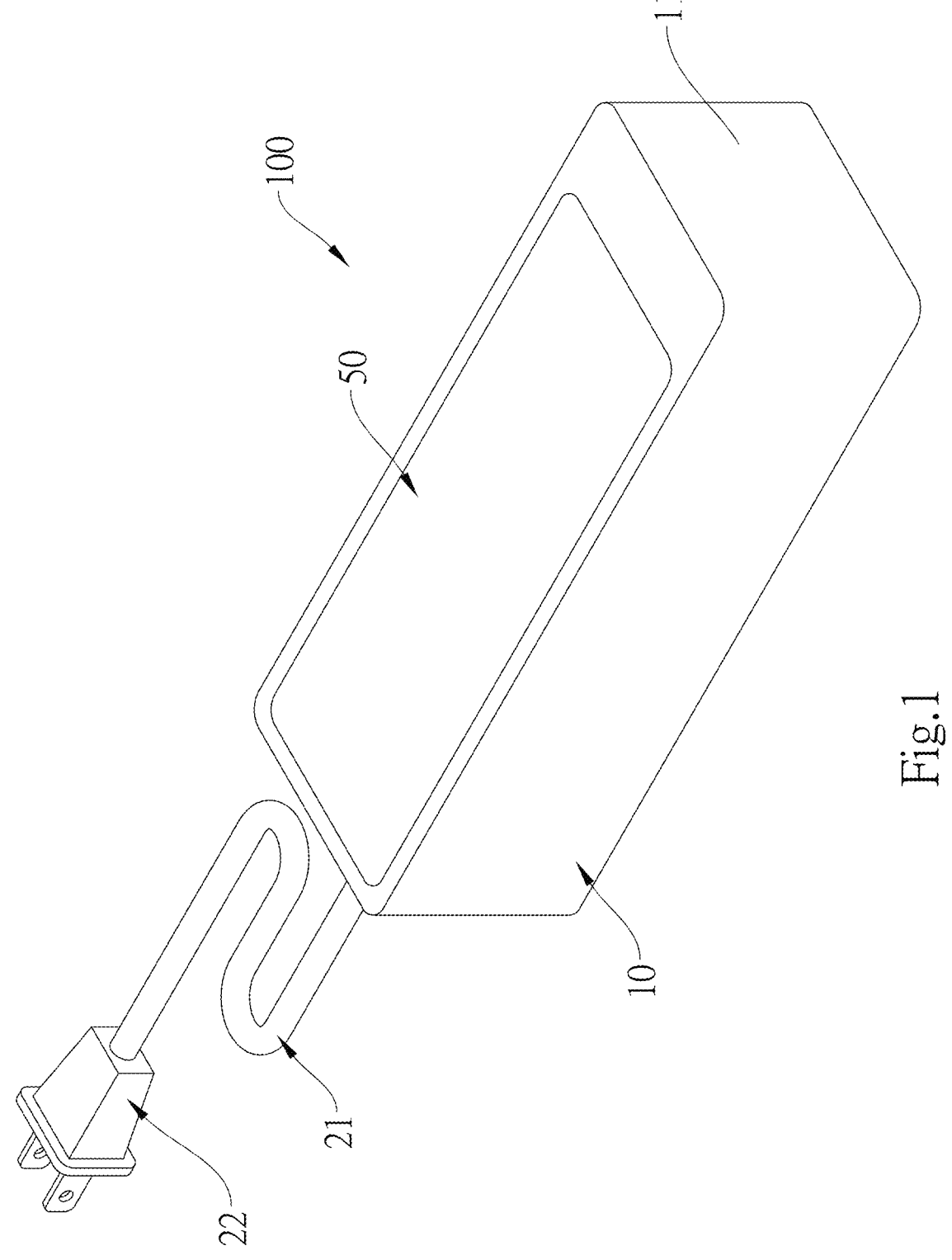
FIG. 1 is a three-dimensional schematic diagram of a negative potential generating device according to one embodiment of the present disclosure.
Figure 2:
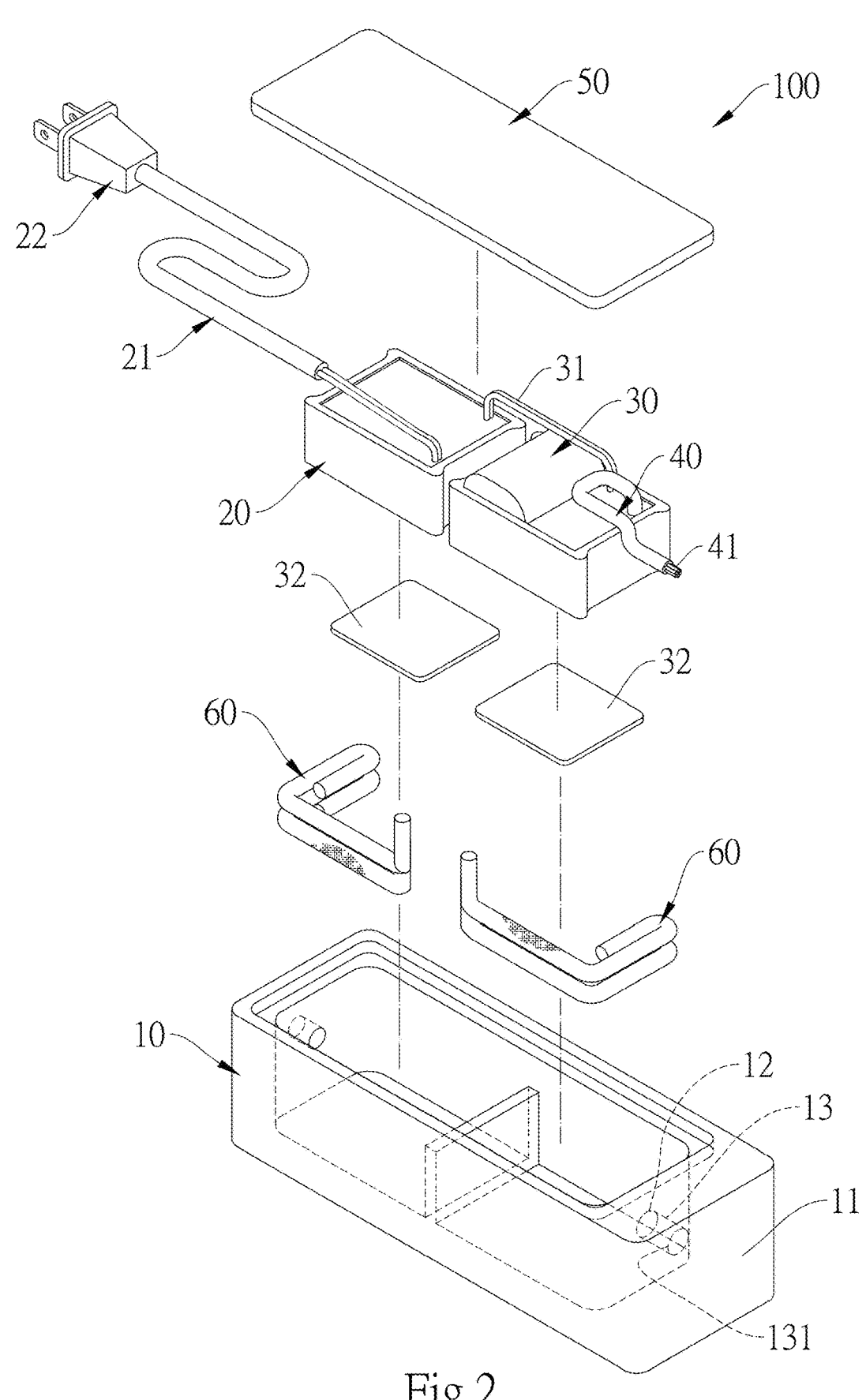
FIG. 2 is an exploded diagram of a negative potential generating device according to one embodiment of the present disclosure.
Figure 3:
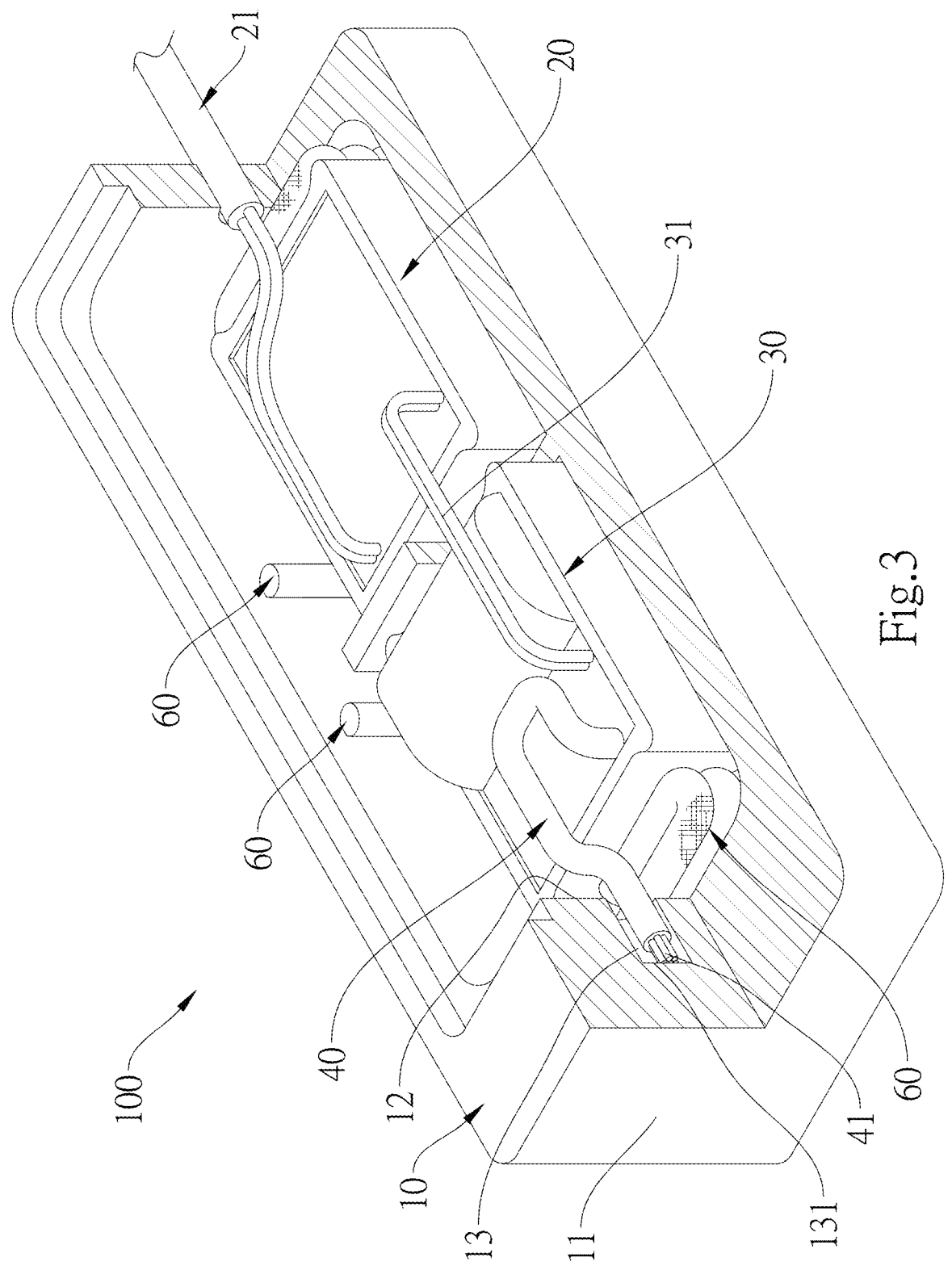
FIG. 3 is a three-dimensional perspective schematic diagram of a negative potential generating device according to one embodiment of the present disclosure, wherein a part of the negative potential generating device is cut open.
Figure 4:
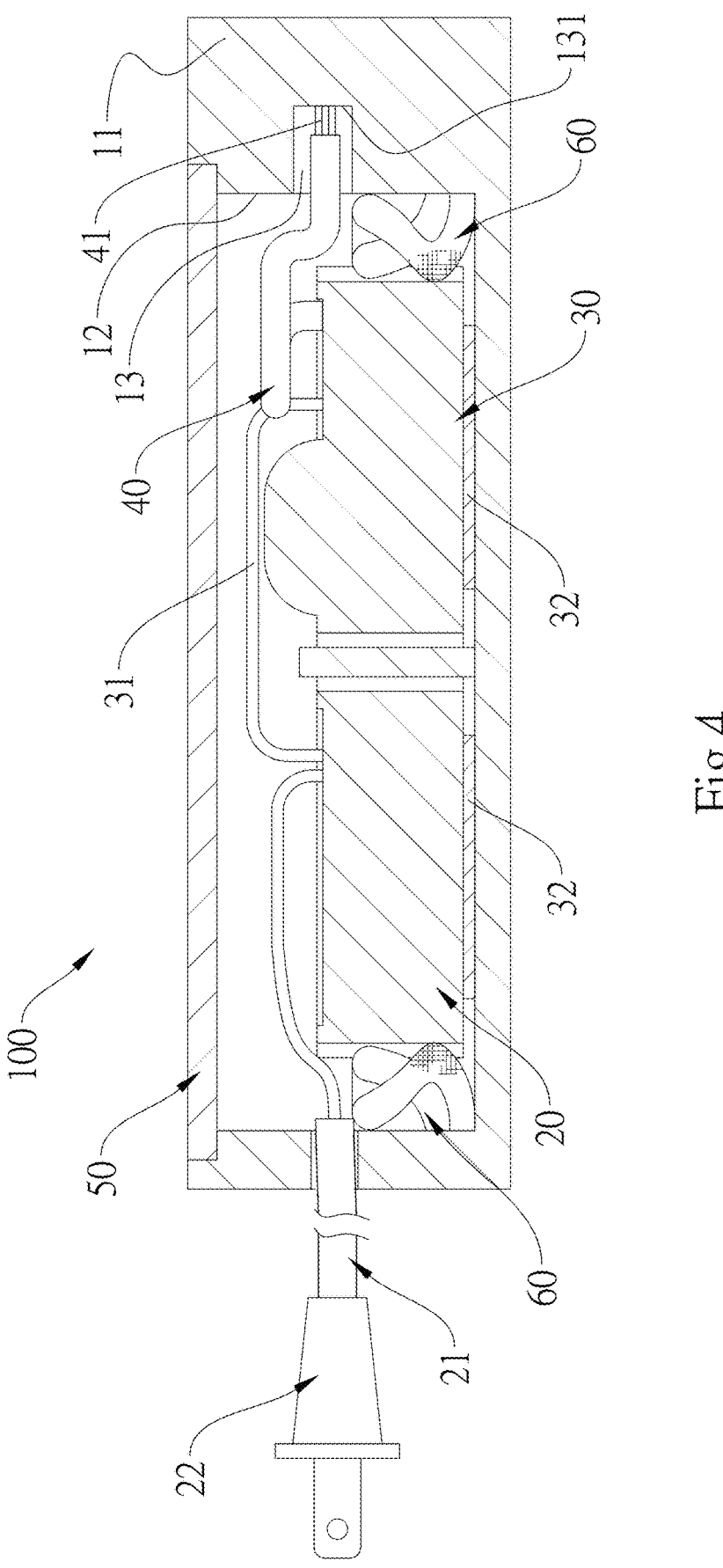
FIG. 4 is a schematic cross-sectional view of a negative potential generating device according to an embodiment of the present disclosure.

Please refer to FIG. 1 to FIG. 4. FIG. 1 is a three-dimensional schematic diagram of a negative potential generating device according to one embodiment of the present disclosure. FIG. 2 is an exploded diagram of a negative potential generating device according to one embodiment of the present disclosure. FIG. 3 is a three-dimensional perspective schematic diagram of a negative potential generating device according to one embodiment of the present disclosure, wherein a part of the negative potential generating device is cut open. FIG. 4 is a schematic cross-sectional view of a negative potential generating device according to an embodiment of the present disclosure.

As shown in the drawings, the negative potential generating device 100 of the present disclosure comprises an insulating box 10, an AC/DC converter 20, a booster 30, a second wire 40, and an insulating lid 50, wherein a core layer of the second wire 40 is a metal wire, and the core layer of the second wire 40 is covered with insulating material.

The insulating box 10 has a side wall 11. An inner surface 12 of the side wall 11 has a blind hole 13, and the opening of the blind hole 13 faces the inside of the insulating box 10. The insulating lid 50 can cover the insulating box 10, and selectively seal the insulating box 10 to isolate the air inside of the insulating box 10 from the air outside the insulating box 10. In some embodiments, the insulating box 10 and the insulating lid 50 are made of wooden material.

The AC/DC converter 20 can be arranged in the insulating box 10, and electrically connected with a plug 22 through a first wire 21, wherein a core layer of the first wire 21 is a metal wire, and the core layer of the first wire 21 is covered with insulating material.

The booster 30 can be arranged in the insulating box 10, and can be electrically connected with the AC/DC converter 20 through a third wire 31, wherein a core layer of the third wire 31 is a metal wire, and the core layer of the third wire 31 is covered with insulating material. In some embodiments, the AC/DC converter 20 and booster 30 are fixed within the insulating box 10 through an adhesive member 32. Preferably, the adhesive member 32 may be 3M® double-sided tape, and the present disclosure is not limited thereto.

One end of the second wire 40 is electrically connected with the booster 30, and the other end of the second wire 40 is inserted into the blind hole 13 and contacts an inner wall surface 131 of the blind hole 13. That is, a metal wire 41 of said other end of the second wire 40 inserted into the blind hole 13 is exposed and directly contacts the inner wall surface 131 of the blind hole 13.

In some embodiments, a plurality of cotton threads 60 are filled into the space between the insulating box 10, the AC/DC converter 20 and booster 30 to prevent the AC/DC converter 20 and booster 30 from swaying.

Figure 5:
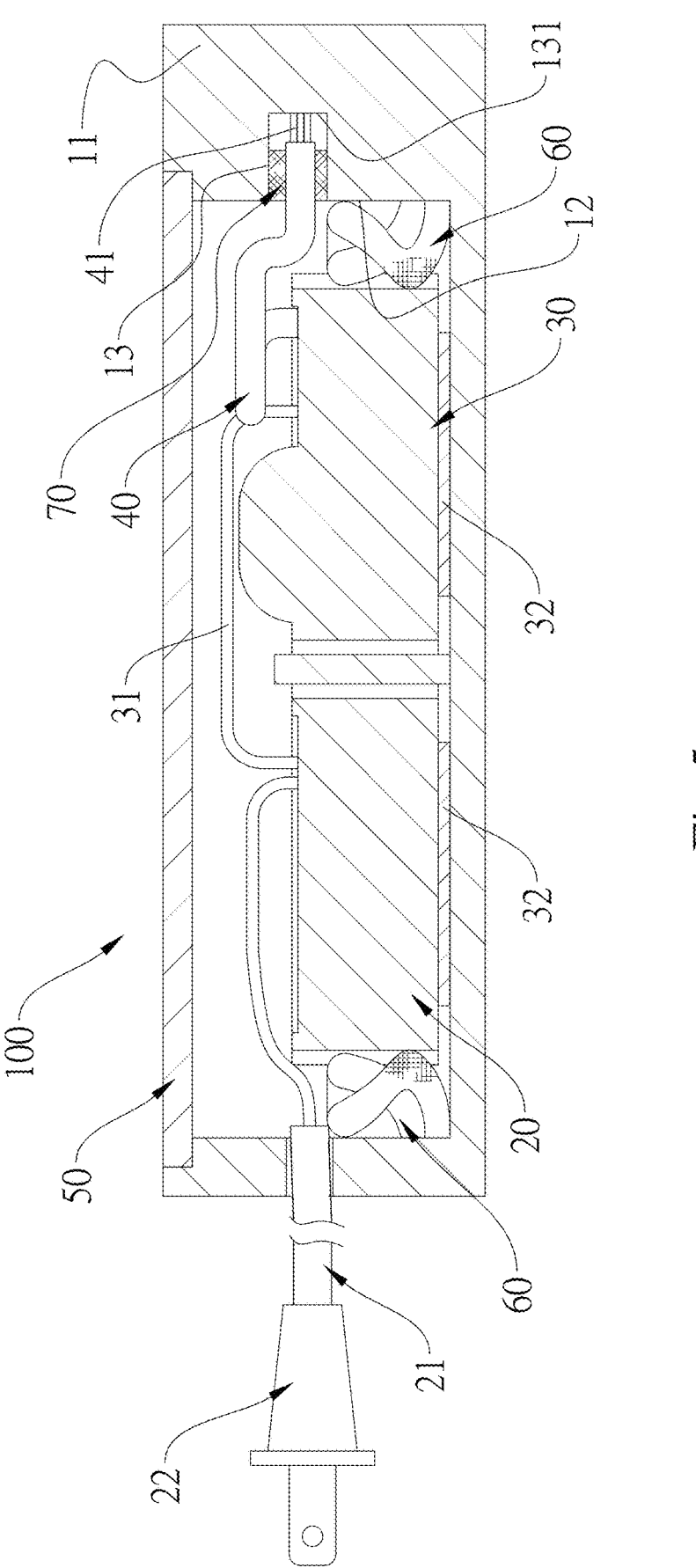
FIG. 5 is a schematic cross-sectional view of a negative potential generating device according to another embodiment of the present disclosure.

Refer to FIG. 5, and FIG. 5 is a schematic cross-sectional view of a negative potential generating device according to another embodiment of the present disclosure. In some embodiments, as shown in FIG. 5, a filling or plugging member 70 is filled or plugged between the second wire 40 and the blind hole 13 to stably fix the second wire 40 in the blind hole 13, and to prevent the second wire 40 from slipping out of the blind hole 13 or swaying in the blind hole 13.

Figure 7:
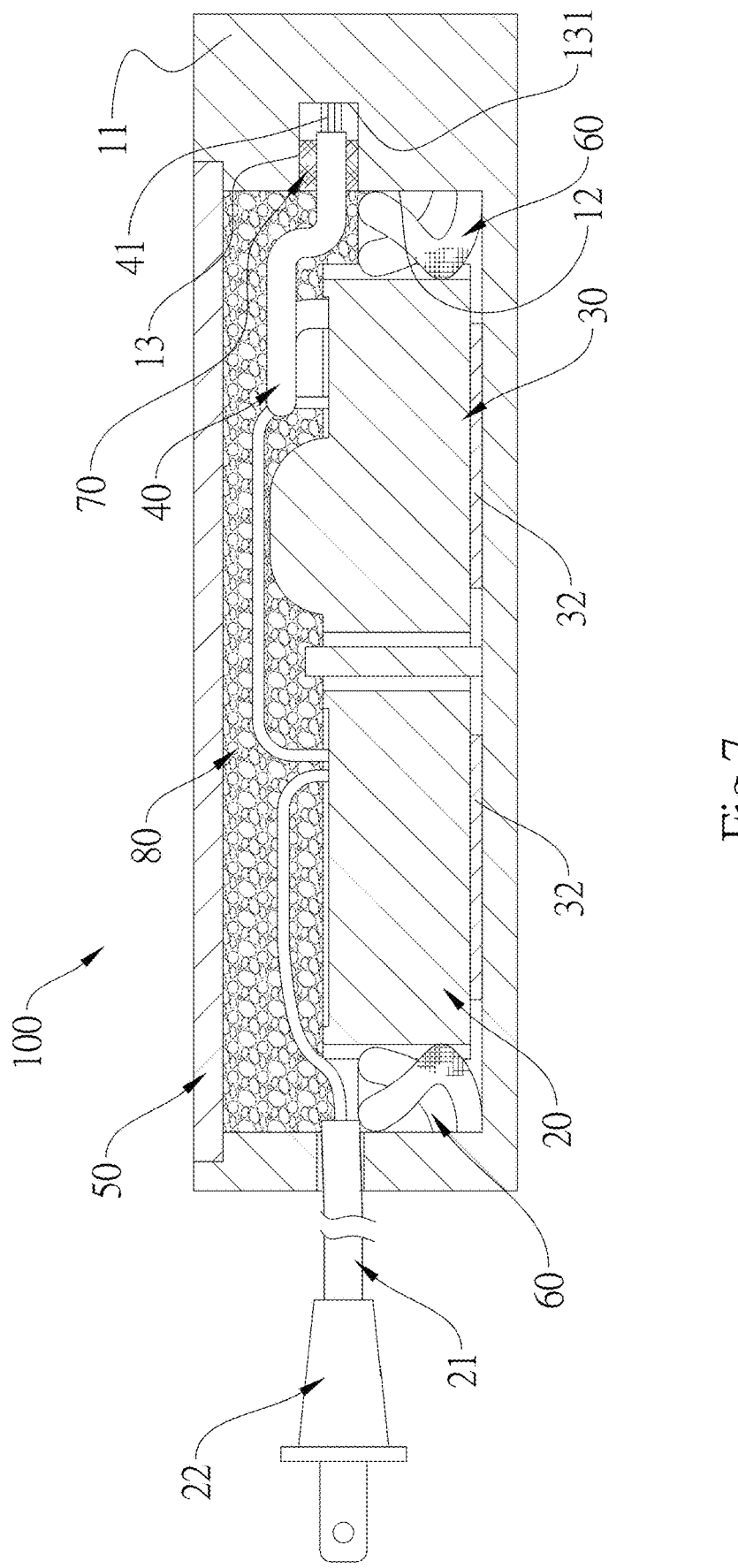
FIG. 7 is a schematic diagram of a negative potential generating device with an insulating box filled with grapheme according to an embodiment of the present disclosure.

Refer to FIG. 7, and FIG. 7 is a schematic diagram of a negative potential generating device with an insulating box filled with grapheme according to an embodiment of the present disclosure. In some embodiments, as shown in FIG. 7, another space between the insulating box 10, the AC/DC converter 20, the booster 30 and the cotton threads 60 is filled with grapheme 80 to shield the electromagnetic waves of the AC/DC converter 20 and the booster 30, so as to prevent the human body from being affected by the electromagnetic waves.

Figure 6:
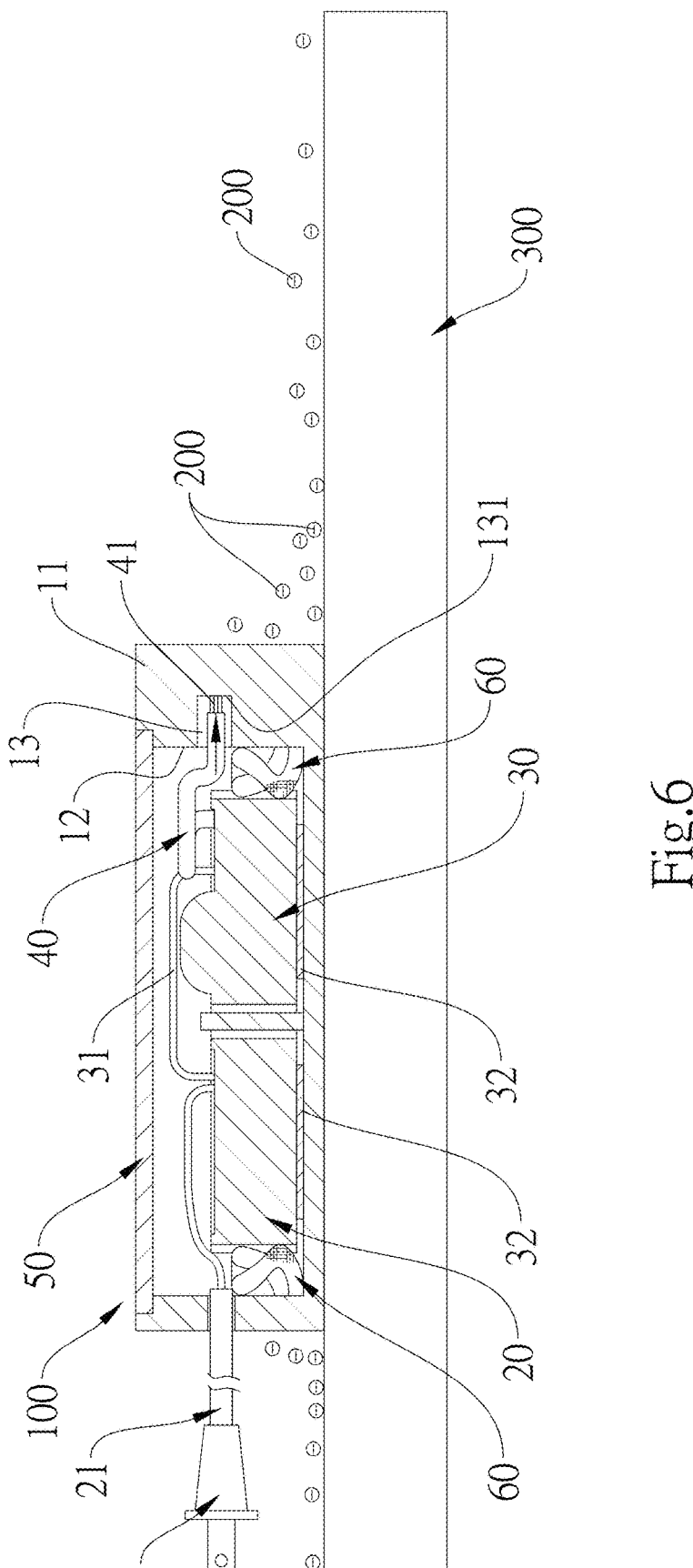
FIG. 6 is a schematic usage diagram of a negative potential generating device according to an embodiment of the present disclosure.

Refer to FIG. 6, and FIG. 6 is a schematic usage diagram of a negative potential generating device according to an embodiment of the present disclosure. When the plug 22 is plugged into or connected to a power source which can be alternating current (AC) power such as utility power, the AC power passes through the first wire 21 to the AC/DC converter 20 to convert the AC power into direct current (DC) power. The DC power then passes through the third wire 31 to the booster 30 for boosting to 8000 volts, for example. Then, the high DC power passes through the second wire 40. As the insulating box 10 is not electrically conductive, the DC power goes to the metal wire 41 of said other end of the second wire 40 inserted to the blind hole 13 for tip discharging, which makes the positive charges accumulate in the blind hole 13. Then, the positive charges in the blind hole 13 will attract the negative charges in the insulating box 10, so that the surroundings of the insulating box 10 near the outside environment is surrounded by positive charges, so that the insulating box 10 is electrically polarized. Therefore, all the negative charges outside the insulating box 10 will be attracted to the insulating box 10, thereby generating a negative potential.

When the negative potential generating device 100 of the present disclosure contacts or is close to a desktop 300 or a human body (not shown), the negative potential 200 will be generated on the desktop 300 or the human body. Since the metal wire 41 of the second wire 40 contacts the inner wall surface 131 of the blind hole 13, it is unlike the case of Document 1 that generates negative ions when the metal wire is exposed to the air in the insulating box. As can be seen from the above, the present disclosure mainly generates negative potential rather than negative ions. Moreover, as the insulating lid 50 can cover the insulating box 10 and can selectively seal the insulating box 10 so as to isolate the air inside of the insulating box 10 from the air outside the insulating box 10, even if pollutants such as ozone or nitric oxide are generated, the pollutants will not be passed outside the insulating box 10 to form another environmental pollution harmful to the human body. In addition, the filling or plugging member 70 can also reduce the amount of air in the blind hole 13, thereby reducing the possibility of generating negative ions and ozone or nitric oxide pollutants.

With the above structure, the negative potential generating device 100 of the present disclosure is easy to carry and can generate the negative potential 200 anytime and anywhere after being connected to the power supply, making it easier and more convenient in use. Furthermore, with the setting arrangement of the grapheme 80, the electromagnetic waves can be shielded while the negative potential generating device 100 is operating, thus the human body, other objects or electrical appliances can be prevented from being affected.

The above is only a detailed description of the present disclosure through preferred embodiments. Simple modifications and changes made to the embodiments shall fall within the spirit and scope of the present disclosure.

The invention claimed is:

1. A negative potential generating device, comprising:
an insulating box with a side wall, wherein an inner surface of the side wall has a blind hole;
an alternating current/direct current (AC/DC) converter arranged inside the insulating box and electrically connected with a plug through a first wire;
a booster arranged inside the insulating box and electrically connected with the AC/DC converter;
a second wire, one side of the second wire is electrically connected with the booster, another side of the second wire is exposed and inserted into the blind hole and contacts with an inner wall surface of the blind hole; and
an insulating lid covering the insulating box.

2. The negative potential generating device according to claim 1, wherein the insulating box and the insulating lid are made of wooden material.

3. The negative potential generating device according to claim 2, wherein the insulating lid covers the insulating box, so that the insulating box is sealed and air inside the insulating box is isolated from air outside the insulating box.

4. The negative potential generating device according to claim 3, wherein a space between the insulating box, the AC/DC converter and the booster is filled with a plurality of cotton threads.

5. The negative potential generating device according to claim 4, wherein the AC/DC converter and the booster are fixed in the insulating box through an adhesive member.

6. The negative potential generating device according to claim 5, wherein a filling or plugging member is filled or plugged between the second wire and the blind hole.

7. The negative potential generating device according to claim 6, wherein another space between the insulating box, the AC/DC converter, the booster and the cotton threads is filled with grapheme.

* * * * *